US008702690B2

(12) United States Patent
Paul et al.

(10) Patent No.: US 8,702,690 B2
(45) Date of Patent: Apr. 22, 2014

(54) DEVICE AND METHOD FOR REAL-TIME LESION ESTIMATION DURING ABLATION

(75) Inventors: Saurav Paul, Minnetonka, MN (US); Hong Cao, Savage, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 892 days.

(21) Appl. No.: 12/742,485

(22) PCT Filed: Nov. 17, 2008

(86) PCT No.: PCT/US2008/083828
§ 371 (c)(1),
(2), (4) Date: May 12, 2010

(87) PCT Pub. No.: WO2009/065140
PCT Pub. Date: May 22, 2009

(65) Prior Publication Data
US 2010/0274239 A1    Oct. 28, 2010

Related U.S. Application Data

(60) Provisional application No. 60/988,734, filed on Nov. 16, 2007.

(51) Int. Cl.
*A61B 18/14* (2006.01)
(52) U.S. Cl.
USPC .................................. 606/33; 606/34; 606/41
(58) Field of Classification Search
USPC ..................... 606/32–35, 41, 48–50
See application file for complete search history.

(56) References Cited

U.S. PATENT DOCUMENTS

| | | | |
|---|---|---|---|
| 6,398,779 B1 * | 6/2002 | Buysse et al. ................. | 606/34 |
| 6,402,742 B1 * | 6/2002 | Blewett et al. ................ | 606/34 |
| 6,423,057 B1 * | 7/2002 | He et al. ........................ | 606/34 |
| 7,066,933 B2 * | 6/2006 | Hagg ............................. | 606/34 |
| 7,282,049 B2 | 10/2007 | Orszulak et al. | |
| 2002/0068931 A1 | 6/2002 | Wong et al. | |
| 2003/0236487 A1 | 12/2003 | Knowlton et al. | |

(Continued)

FOREIGN PATENT DOCUMENTS

WO    WO-2007067628    6/2007

OTHER PUBLICATIONS

Bosnos, Michael "Assessment of Myocardial Lesion Size during In Vitro Radio Frequency Catheter Ablation", *IEEE Transactions on Biomedical Engineering*. vol. 50, No. 6 Jun. 2003, 768-776.

(Continued)

*Primary Examiner* — Michael Peffley
(74) *Attorney, Agent, or Firm* — Wiley Rein LLP

(57) ABSTRACT

Disclosed herein are ablation systems and methods for providing feedback on lesion formation in real-time. The methods and systems assess absorptivity of tissue based on a degree of electric coupling or contact between an ablation electrode and the tissue. The absorptivity can then be used, along with other information, including, power levels and activation times, to provide real-time feedback on the lesions being created. Feedback may be provided, for example, in the form of estimated lesion volumes and other lesion characteristics. The methods and systems can provide estimated treatment times to achieve a desired lesion characteristic for a given degree of contact, as well as depth of a lesion being created. The degree of contact may be measured using different techniques, including the phase angle techniques and a coupling index.

15 Claims, 6 Drawing Sheets

(56) References Cited

U.S. PATENT DOCUMENTS

2005/0113819 A1* 5/2005 Wham et al. .................. 606/34
2007/0049915 A1* 3/2007 Haemmerich et al. .......... 606/32
2007/0123847 A1* 5/2007 Mihori ........................... 606/34

OTHER PUBLICATIONS

Hoffmann, Ellen "Biophysical parameters of radiofrequency catheter ablation", *International Journal of Cardiology*, vol. 37, No. 2 Nov. 1992, Abstract only.

* cited by examiner

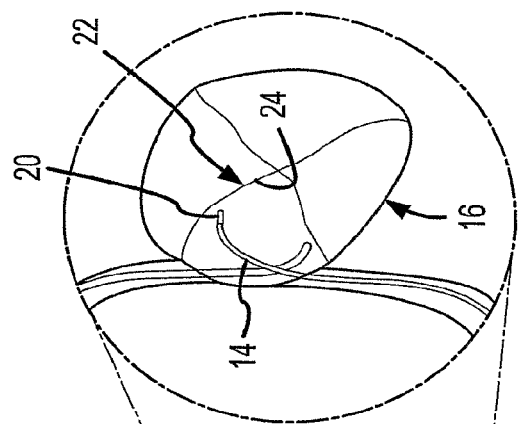
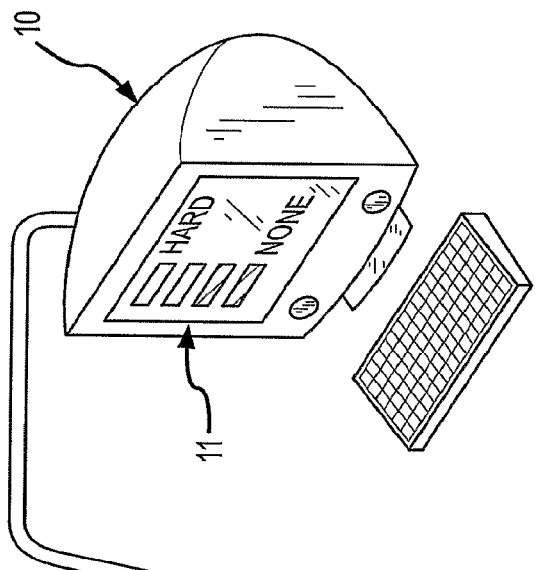
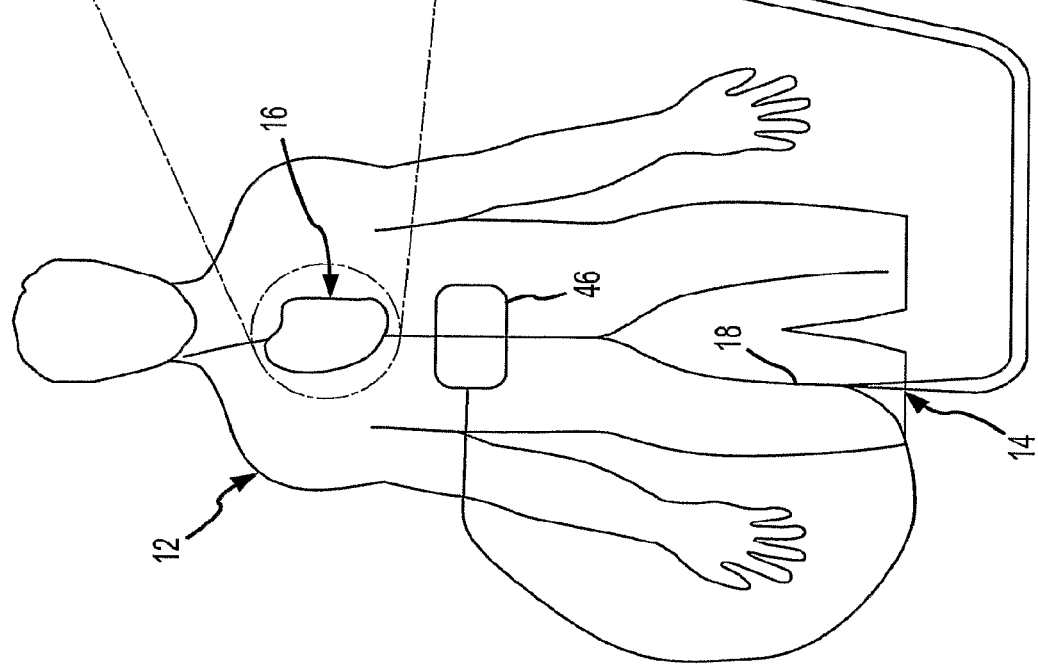
FIG. 1a
FIG. 1

DEVICE AND METHOD FOR REAL-TIME LESION ESTIMATION DURING ABLATION

CROSS-REFERENCE TO RELATED APPLICATIONS

This application is a national stage filing based upon international application no. PCT/US2008/083828 (the '828 application), filed 17 Nov. 2008, which claims the benefit of and priority to U.S. provisional application No. 60/988,734, filed 16 Nov. 2007 (the '734 application). The '828 application and '734 application are both hereby incorporated by reference as though fully set forth herein.

BACKGROUND OF THE INVENTION a. Field of the Invention

The present invention relates generally to an ablation catheter and method for estimating lesion characteristics as the lesion is being formed.

b. Background

Catheters are used for an ever growing number of medical procedures. To name just a few examples, catheters are used for diagnostic, therapeutic, and ablation procedures. Typically, the user manually manipulates the catheter through the patient's vasculature to the intended site, such as a site within the patient's heart. The catheter typically carries one or more electrodes or other diagnostic or therapeutic devices, which may be used for ablation, diagnosis, cardiac mapping, or the like.

It is well known to utilize catheters for ablation treatments. For example, catheters may be used to accomplish radiofrequency (RF) ablation by transmission of RF energy to a desired target area through an electrode assembly to ablate tissue at the target site. RF energy may generate significant heat, which if not controlled, can result in excessive tissue damage, such as steam pop, tissue charring, and the like. Accordingly, a need exists to control the delivery of RF energy and to prevent undesired tissue damage.

Surgical devices and techniques utilizing electrodes to transfer therapeutic energy to tissue are well known. Electrosurgery allows for the incision, cauterization, fulguration, and desiccation of tissue through the application of high-power, radio frequency (RF) energy to tissue through an electrode. Ablation techniques, whereby the target tissue is necrotized through coagulation, are also performed using surgical devices with electrodes to transfer RF energy to tissue. Many benefits may be gained by forming lesions in tissue—for example, control of cardiac arrhythmia or tachycardia, removal of skin diseases, or the treatment of varicose veins—if the depth and location of the lesions being formed can be controlled. In particular, it can be desirable to elevate tissue temperature to around 50-55° C. until lesions are formed via coagulation necrosis, which changes the electrical properties of the tissue. For example, when sufficiently deep lesions are formed at specific locations in cardiac tissue via coagulation necrosis, undesirable ventricular tachycardia may be lessened or eliminated. "Sufficiently deep" lesions means transmural lesions in some cardiac applications.

Several difficulties may be encountered, however, when attempting to form adequately-deep lesions at specific locations using some existing surgical ablation electrodes. For example, when forming lesions with RF energy, high temperature gradients are often encountered in the vicinity of the electrode. At the edges of some existing electrodes are regions of very high current density leading to large temperature gradients and hot spots. These "edge effects" may result in the formation of undesirable coagulum and charring of the surface tissue. For example, undesirable coagulum may begin to form when blood reaches around 80° C. for an appreciable length of time, and undesirable tissue charring and desiccation may be seen when tissue reaches around 100° C. for an appreciable length of time. There two types of undesirable coagulum: coagulum that adheres to and damages the medical device; and coagulum blood clots or curds that may enter a patient's bloodstream, possibly resulting in other health problems for the patient. Charring of the surface tissue may also have deleterious effects on a patient.

As the temperature of the electrode is increased, the contact time required to form an adequately-deep lesion decreases, but the likelihood of charring surface tissue and forming undesirable coagulum increases. As the temperature of the electrode is decreased, the contact time required to form an adequately-deep lesion increases, but the likelihood of charring surface tissue and forming undesirable coagulum decreases. It is, therefore, a balancing act trying to ensure that tissue temperatures are adequately high for long enough to create deep lesions, while still preventing or minimizing coagulum formation and/or charring of the surface tissue.

Generally, a need exists to control the delivery of ablation energy (for example, RF energy) and to provide feedback on size and other lesion characteristics during the ablation process.

The information included in this background section of the specification, including any references cited herein and any description or discussion thereof, is included for technical reference purposes only and is not to be regarded subject matter by which the scope of the invention is to be bound.

BRIEF SUMMARY OF THE INVENTION

The present invention is directed to improved ablation catheters and methods useful in conjunction with such ablation catheters.

The present invention provides for an ablation catheter for use in controlling the delivery of ablation energy during the ablating process. In one aspect, the invention provides for an ablation system for ablating tissue in need of treatment, comprising: an ablation catheter having at least one electrode; a power source coupled to at least one electrode, said power source being programmable to deliver at least one programmable level of power; a voltage measurement device for measuring a voltage signal being delivered to the tissue; a current measurement device for measuring a current signal being delivered to the tissue; a phase measurement device to determine an amount of phase change between the measured voltage signal and the measured current signal; a clock to measure a time period during which ablative power is delivered by the power source; and a lesion analysis processor for estimating lesion formation. Preferably, the lesion analysis processor estimates lesion formation as a function of at least: the measured phase change between the voltage signal and the current signal; information indicating the programmable power level at which the power source delivers ablative power to tissue in need of treatment; and the measured time period for which ablative power is delivered by the ablation catheter to tissue in need of treatment. Optionally, the system includes a controller coupled to the power source and the lesion analysis processor for controlling the power source based on information provided by the lesion analysis processor. Optionally, the ablation system includes a tissue temperature measurement device to measure a temperature of the tissue being ablated, and the controller may be coupled to the tissue temperature measurement device such that if the temperature of the tissue being ablated exceeds a maximum desirable temperature, the controller will deactivate the ablation source. In an exemplary embodiment, the power source is an RF power source, in which case the lesion analysis processor can estimate lesion formation as a function based on the measured phase change between an RF voltage signal and an RF current signal at the point in time when the RF power source is initially activated. In another exemplary embodiment, the ablation system has a lesion analysis processor that estimates lesion formation as a function based on the measured phase change between the voltage signal and the current signal at the point during treatment when the lesion is being estimated.

The ablation system may have a single power source operating with one or more electrodes, in which case, the power source is preferably programmable to deliver assessment power, at a level that is below an ablation power level, to assess the degree of contact between the catheter and the tissue being treated. The single power source can also be programmed or controlled to deliver ablation energy to the tissue in need of treatment, through the same electrode as assessment is done, or through a different electrode.

While the degree of contact or electric coupling can be measured using the phase angle that exists between the measured voltage signal and measured current signal of the assessment voltage, other measurements can be used as well. For example, the complex impedance, which is the complex sum of resistance and reactance, can be measured and used. In particular, the phase angle of the complex impedance is the same phase angle that would be measured by comparing the voltage signal to the current signal. Either technique could be used.

In another embodiment, an alternative to measuring the phase angle can be used. For example, a coupling index indicative of a degree of contact between an electrode and a tissue can be used. The coupling index can be calculated from the components of complex impedance, such as resistance, reactance, impedance magnitude, and impedance phase angle.

In another embodiment, the ablation system of the present invention may utilize a first power source coupled to a first electrode to deliver ablation energy to the tissue, and a second power source coupled to a second electrode on the catheter to deliver assessment power which will be measured by the voltage measurement device and the current measurement device to assess the degree of contact between the second electrode and the tissue.

Preferably, the lesion analysis processor utilizes a regression analysis of a plurality of previously collected data points to calculate an absorptivity factor for the tissue being ablated. Each of the plurality of previously collected data points comprises information respectively for a plurality of lesions, including at least a degree of tissue-electrode contact, a lesion volume, and an ablation power level. The lesion analysis processor can calculate a lesion volume for a lesion being created based on a measured amount of phase change, a programmed level of ablation power being used to create the lesion; and a time period measured by the clock indicating the time for which the ablation treatment has been active. Optionally, the controller can be programmed to continue delivering ablation power if the lesion analysis processor determines that the calculated lesion volume for the lesion being created is less than a desired lesion volume. The controller can also be programmed to continue delivering ablation power if the lesion analysis processor determines that the calculated lesion volume for the lesion being created is less than a desired lesion volume.

Also disclosed herein is a method of providing feedback on lesion formation, in which the an ablation catheter is placed in contact with tissue to be ablated. The catheter can have a tissue-contacting ablation electrode coupled to an RF energy source for delivering energy to the tissue. The RF energy source is activated to apply RF power at a first power level, so that an RF voltage signal can be delivered to the tissue by the tissue-contacting ablation electrode. The RF current signal being delivered to the tissue by the tissue-contacting ablation electrode can be measured, and a degree of electrode-tissue contact can be assessed by determining an amount of phase change between the RF voltage signal and the RF current signal at a point in time before the temperature of the tissue is increased by an application of ablation energy. A regression analysis curve can be created to provide information on absorptivity factors as a function of phase change between an RF voltage signal and an RF current signal. The regression analysis curve can be used to determine an absorptivity factor corresponding to the determined amount of phase change between the RF voltage and the RF current. The RF energy source can be activated to apply RF power at a second power level to deliver an amount of RF energy effective for ablating tissue. The time for which the RF energy source is activated at the second power level can be monitored, and feedback can be provided to an operator by providing information on the lesion volume as a function of the determined absorptivity factor, the second power level, and the time for which the RF energy source is activated at the second power level.

Preferably, the regression analysis is generated using a collection of data points for a plurality of lesions created using a plurality of different degrees of applied contact. Each of the data points is preferably generated by: placing the ablation catheter into contact with tissue to be ablated and achieving a respective degree of applied contact between the ablation catheter and the tissue, applying RF power at a power level L1 at the respective degree of applied contact; measuring an RF voltage signal being delivered to the tissue; measuring an RF current signal being delivered to the tissue; determining a respective amount of phase change between the measured RF voltage signal and RF current signal at a point in time before the temperature of the tissue is increased by an application of ablation energy; applying RF power at a power level L2 for a time period TP1 at the respective degree of applied contact to create a lesion; measuring the respective lesion volume of the lesion resulting from the application of RF power at power level L2 for a time period TP1 at the respective degree of applied contact; and associating the measured respective lesion volume, the measured respective amount of phase change, power level L2, and time period TP1 to form a respective data point. The regression analysis can then be used determine absorptivity as a function of changes in phase angle between an RF voltage signal and an RF current signal. Preferably, the power level L1 is below a level that would be effective to ablate tissue, and the power level L2 is at a level that would be effective to ablate tissue, though it is also possible that the power level L1 is about the same level as power level L2, and each of L1 and L2 are at a level that would be effective to ablate tissue.

In exemplary embodiments, feedback can be provided using a display, including without limitation, a computer screen and/or a numeric or analog display. The display can provide information on a calculated lesion volume for the lesion being created and/or information on a target lesion volume. If the calculated lesion volume equals or exceeds the target lesion volume, the ablation energy source can be deactivated.

In another embodiment, temperature of the tissue being ablated can be monitored and the ablation energy source can be deactivated if the tissue temperature exceeds a target tissue temperature.

The various embodiments can be utilized with ablation sources that operate in a constant power mode, where the amount of power being delivered is substantially constant over a period of time, or with ablation sources that operate in a temperate control mode, in which case, the power may fluctuate over time and will be deactivated when the tissue temperature meets a preset level.

Also disclosed is a method of estimating lesion size. The method includes placing an ablation catheter in contact with tissue to be ablated, said catheter having a tissue-contacting ablation electrode coupled to an ablation energy source for delivering ablation energy to the tissue and a contact-assessing electrode coupled to a contact-assessing energy source for delivering contact-assessing energy to the tissue. The contact-assessing energy source is activated to deliver a contact-assessing energy, and the contact-assessing voltage signal being delivered to the tissue by the contact-assessing electrode is measured along with the contact-assessing current signal being delivered to the tissue by the contact-assessing electrode. The amount of phase change between the contact-assessing voltage signal and the contact-assessing current signal is determined, which is indicative of the degree of electric coupling or contact. The ablation energy source is activated to apply ablation energy to the tissue at a preset power level, and the temperature of the tissue being ablated is monitored so that if the monitored tissue temperature exceeds a maximum desired tissue temperature, the ablation energy source can be deactivated. The size of the lesion being created can be estimated using at least the following: i) the determined amount of phase change between the contact-assessing voltage signal and the contact-assessing current signal; ii) the preset power level; and iii) the time for which the ablation energy source is activated.

The ablation energy source being used can be separate from or the same source as is used for the contact-assessing energy source. When there is a single source, the single source preferably is programmable to deliver non-ablative power for assessing a degree of contact between the contact-assessing electrode and the tissue to be ablated, and to deliver an ablative power for ablation.

Exemplary methods disclosed herein may also use regression analysis to help provide feedback on lesion formation. For example, a validation study may be used to create a plurality of lesions, each of which may be measured and studied to create data points for use in a regression analysis. Preferably, the plurality of lesions are created using varying degrees of contact. For each lesion, the degree of contact can be assessed, the volume of the lesion created can be measured and a recording system can be used to record the measured data and the settings used to create each of the plurality of lesions. A regression analysis can then be run on the collection of data stored in the recording system to estimate absorptivity factors for tissue being ablated. The regression analysis can then be used to estimate lesion size using at least the following: i) the determined amount of phase change between the contact-assessing voltage signal and the contact-assessing current signal; ii) the preset power level; iii) the time for which the ablation energy source is activated; and iv) a estimated absorptivity factor determined using the regression analysis.

According to another aspect of the present invention, an ablation system for ablating tissue in need of treatment generally includes: an ablation catheter having at least one electrode; a power source coupled to at least one electrode, the power source being programmable to deliver at least one programmable level of power; a voltage measurement device for measuring a voltage signal being delivered to the tissue; a current measurement device for measuring a current signal being delivered to the tissue; a contact assessment device that assesses a degree of electrical coupling or contact between the ablation catheter and tissue being treated by determining an amount of phase change between the measured voltage signal and the measured current signal; a clock to measure a time period during which ablative power is delivered by the power source; a power monitoring device to monitor the amount of ablation power that is delivered by the ablation catheter; a temperature sensor to measure the temperature of the tissue being treated and to monitor for changes over time; a lesion analysis processor for estimating lesion formation as a function of at least: i) a output of the contact assessment device that corresponds to an amount of phase change between the measured voltage signal and the measured current signal at a point in time before the temperature of the tissue increases from application of ablation energy; ii) information from the power monitoring device indicative of the amount of ablation power that is delivered by the ablation catheter as a function of time; iii) information from the temperature sensor indicative of the changes in temperature of the tissue being treated with ablation energy; and a controller coupled to the power source and the lesion analysis processor for controlling the power source based on information provided by the lesion analysis processor.

Optionally, the controller may be coupled to the tissue temperature measurement device such that, if the temperature of the tissue being ablated exceeds a maximum desirable temperature, the controller will deactivate the power source.

The lesion analysis processor may include a look up table or graph of a regression analysis of previously measured lesion volumes for a plurality of lesions. This data may be used by the lesion analysis processor to calculate an absorptivity factor for the tissue being ablated, and this absorptivity factor may also be used by the lesion analysis processor to estimate lesion formation.

It is also contemplated that the controller may be programmed to operate the power supply at a first power level to allow the system to assess electrical coupling or contact between the catheter and the tissue and a second power level to ablate tissue.

Also disclosed herein is a method of ablating tissue including the following steps: electrically coupling an ablation catheter with tissue to be ablated, the catheter having a tissue-contacting ablation electrode coupled to an RF energy source for delivering power to the tissue; activating the RF energy source to supply RF power at a first power level; monitoring an RF voltage signal being delivered to the tissue; monitoring an RF current signal being delivered to the tissue; monitoring an amount of phase change between the RF voltage signal and RF current signal while RF power is being delivered to the tissue; activating the RF energy source to supply RF power at a second power level; monitoring a temperature of the tissue to which RF power is being applied; obtaining a regression analysis curve that provides information on absorptivity factors as a function of at least a) a phase change between an RF voltage signal and an RF current signal, where the phase change is indicative of a degree of electrical coupling or contact between a catheter and tissue being ablated; and b) a change in tissue temperature that results from applied ablation energy; using the regression analysis curve to determine an absorptivity factor for tissue being ablated, where the regression analysis curve is used to identify the absorptivity based on a) a measured amount of phase change between the RF voltage and the RF current and b) a measured amount of change in tissue temperature which change reflects the application of ablation energy to the tissue; and calculating a lesion volume as a function of the determined absorptivity factor, the difference between the current tissue temperature and the initial tissue temperature, and the total amount of ablation energy delivered to the tissue. The RF energy source may be deactivated if the tissue temperature exceeds a maximum tissue temperature setting. The RF power source may also be deactivated when the calculated lesion volume equals or exceeds a target lesion volume.

The regression analysis curve may be obtained by forming a collection of data points for a plurality of lesions created using a plurality of different degrees of applied electrical coupling or contact. The data points may be measured as follows for each respective lesion of the plurality of lesions: electrically coupling the ablation catheter with tissue to be ablated and achieving a respective degree of applied electrical coupling or contact between the ablation catheter and the tissue; applying RF energy at a power level L1 at the respective degree of applied electrical coupling or contact; measuring an RF voltage signal being delivered to the tissue; measuring an RF current signal being delivered to the tissue; determining a respective amount of phase change between the measured RF voltage signal and RF current signal at a point in time before the temperature of the tissue is increased by an application of ablation energy; applying RF power at a power level L2 at the respective degree of applied electrical coupling or contact to create a lesion; monitoring a temperature of the tissue being ablated; monitoring the time period TP1 for which RF power applied at power level L2 to form a lesion; determining a respective amount of phase change between the measured RF voltage signal and RF current signal after the formation of a lesion; measuring the respective lesion volume of the lesion resulting from the application of RF power at power level L2 for a time period TP1 at the respective degree of applied electrical coupling or contact; associating the measured respective lesion volume, the measured respective amount of phase change prior to any increase in tissue temperature the measured respective amount of phase change after the formation of a lesion, power level L2, and time period TP1 to form a respective data point; and applying a regression analysis to the collection of respective data points to generate a graph or lookup table for determining absorptivity as a function of at least i) a degree of electrical coupling or contact as indicated by changes in phase angle between an RF voltage signal and an RF current signal and ii) a change in tissue temperature that results from application of ablation energy. For example, RF power may be applied at power level L2 until the tissue temperature reaches about 55° C.

According to yet another aspect of the present invention, a method of estimating lesion size generally includes the following steps: placing an ablation catheter in contact with tissue to be ablated; activating the contact-assessing energy source to deliver a contact-assessing energy; measuring a contact-assessing voltage signal being delivered to the tissue by the contact-assessing electrode; measuring a contact-assessing current signal being delivered to the tissue by the contact-assessing electrode; determining an amount of phase change between the contact-assessing voltage signal and the contact-assessing current signal at a point in time before activation of the ablation energy source; activating the ablation energy source to apply ablation energy to the tissue at a preset power level; monitoring the amount of ablation energy delivered by the ablation energy source; monitoring a time period for which ablation energy is being delivered by the ablation source; monitoring a temperature of the tissue being ablated; and estimating a size of the lesion being created using at least the following: i) the determined amount of phase change between the contact-assessing voltage signal and the contact-assessing current signal before activation of the ablation energy source; ii) the monitored amount of ablation power delivered by the ablation energy source; iii) the monitored time period for which the ablation energy source is activated; and iv) the change in temperature of the tissue as measured before activation of the ablation energy and the current tissue temperature. Typically, the catheter will include: a tissue-contacting ablation electrode coupled to an ablation energy source for delivering ablation energy to the tissue and a contact-assessing electrode coupled to a contact-assessing energy source for delivering contact-assessing energy to the tissue. Optionally, the method also includes: determining that the estimated size of the lesion being created is at or near a desired size and deactivating the ablation energy source.

It is desirable for the contact-assessing energy source to be an RF energy source that delivers non-ablative power for assessing a degree of contact between the contact-assessing electrode and the tissue to be ablated. The ablation energy source may also be an RF energy source. In some embodiments of the invention, the tissue-contacting ablation electrode is the contact-assessing electrode, and is coupled to a programmable RF energy source, such that a non-ablative power may be delivered for contact assessment and an ablative power may be delivered for tissue ablation.

Further disclosed is an ablation system for ablating tissue in need of treatment. The system includes: an ablation catheter having at least one electrode to deliver ablation energy to tissue in need of treatment; a variable power source coupled to at least one electrode; a voltage measurement device for measuring a voltage signal being delivered to the tissue; a current measurement device for measuring a current signal being delivered to the tissue; a phase measurement device to determine an amount of phase change between the measured voltage signal and the measured current signal; a power measurement device to measure, as a function of time, the power being delivered by the power source; and a lesion analysis processor for estimating lesion formation as a function of at least: a measured phase change between the voltage signal and the current signal and information indicating an amount of power that is delivered to the tissue. The lesion analysis processor may estimate an amount of treatment time necessary to form a lesion, and may also provide real-time feedback on an estimated depth of a lesion being created using the system.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 1 is a diagrammatic illustration of an exemplary tissue ablation system which may be implemented to assess electrode-tissue contact during a tissue ablation procedure for a patient.

FIG. 1a is a detailed illustration of the patient's heart in FIG. 1, showing the electrode catheter after it has been moved into the patient's heart.

DETAILED DESCRIPTION OF THE INVENTION

Figure 2A:
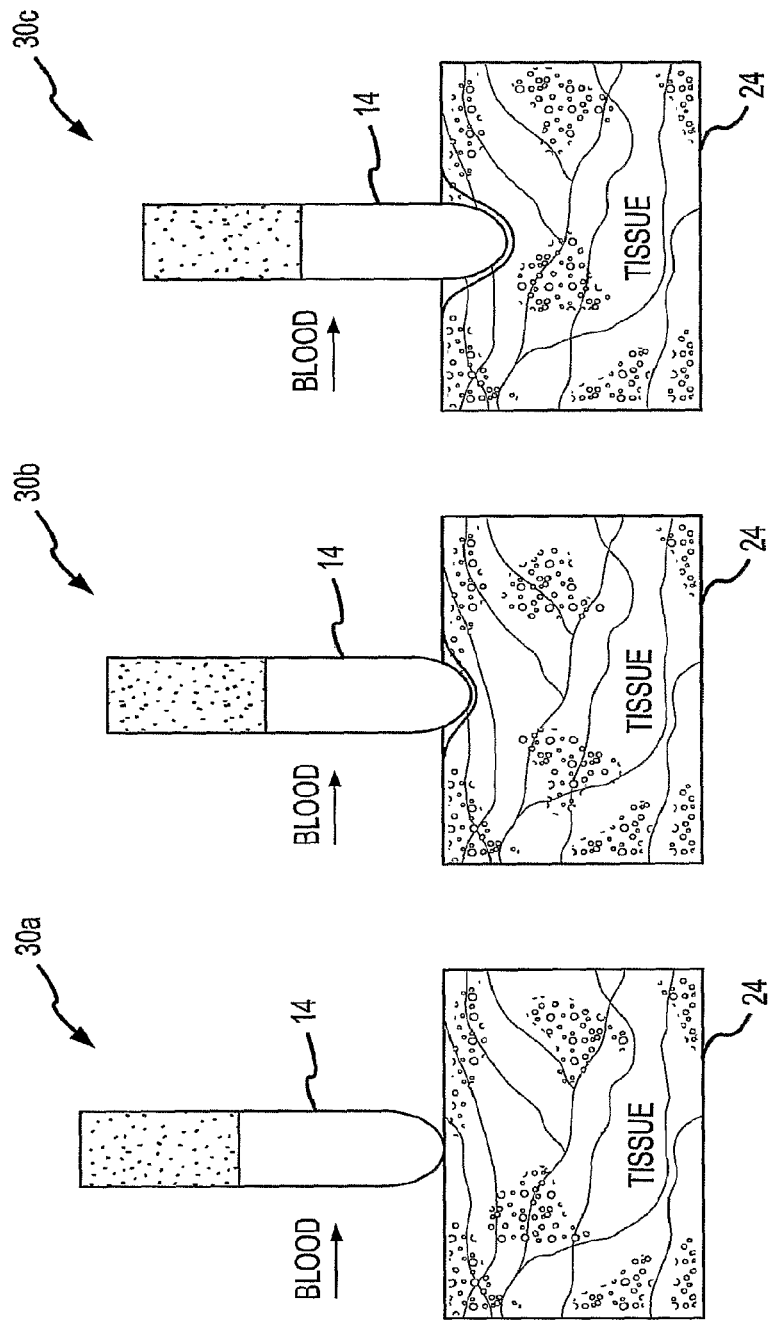
FIG. 2a illustrates exemplary levels of electrical contact or coupling between the electrode catheter and a target tissue.

Exemplary embodiments of a tissue ablation system and methods of use to estimate characteristics of lesions being formed are depicted in the figures. As described further below, the tissue ablation system of the present invention provides a number of advantages, including, for example, the ability to estimate lesion characteristics during the ablation process and thereby reduce the likelihood of complications associated with applying excessive ablative energy to a target tissue. The invention also provides for enhanced lesion estimation and formation.

FIG. 1 is a diagrammatic illustration of an exemplary electrode catheter system 10 which may be implemented to estimate lesion characteristics during a tissue ablation procedure for a patient 12. Catheter system 10 includes an electrode catheter 14, which may be inserted into the patient 12, e.g., for forming ablative lesions inside the patient's heart 16. During an exemplary ablation procedure, a user (e.g., the patient's physician or a technician) may insert the electrode catheter 14 into one of the patient's blood vessels 18, e.g., through the leg (as shown in FIG. 1) or the patient's neck. The user, guided by a real-time fluoroscopy imaging device (not shown) or other localization system, moves the electrode catheter 14 into the patient's heart 16 (as shown in more detail in FIG. 1A).

In a preferred embodiment, the localization/mapping system is the EnSite NavX™ navigation and visualization system of St. Jude Medical, Atrial Fibrillation Division, Inc., which generates the electrical fields for locating a catheter. Other localization systems, however, may be used in connection with the present invention, including for example, the CARTO navigation and location system of Biosense Webster, Inc., or the AURORA® system of Northern Digital Inc., both of which utilize magnetic fields rather than electrical fields. The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

When the electrode catheter 14 reaches the patient's heart 16, electrodes 20 at the tip of the electrode catheter 14 may be implemented to electrically map the myocardium 22 (i.e., muscular tissue in the heart wall) and locate a target tissue 24. After locating the target tissue 24, the user must move the electrode catheter 14 into contact and electrically couple the catheter electrode 20 with the target tissue 24 before applying ablative energy to form an ablative lesion or lesions. For purposes of this application the term "contact" shall mean that the electrode catheter is sufficiently close to the target tissue such that it is electrically coupled to the target tissue and can transfer sufficient ablation energy to form a lesion; in this sense "contact" does not require, but may include, mechanical contact.

The electrode-tissue contact refers to the condition when the catheter electrode 14 physically touches the target tissue 24 thereby causing a mechanical coupling between the catheter electrode 14 and the target tissue 24. Electrical coupling refers to the condition when a sufficient portion of electrical energy passes from the catheter electrode 14 to the target tissue 24 so as to allow efficient lesion creation during ablation. For target tissues with similar electrical and mechanical properties, electrical coupling includes mechanical contact. That is, mechanical contact is a subset of electrical coupling. Thus, the catheter electrode may be substantially electrically coupled with the target tissue without being in mechanical contact. In other words, if the catheter electrode is in mechanical contact, it is also electrically coupled. The range or sensitivity of electrical coupling, however, changes for tissues with different electrical properties. For example, the range of electrical coupling for electrically conductive myocardial tissue is different from the vessel walls. Likewise, the range or sensitivity of electrical coupling also changes for tissues with different mechanical properties, such as tissue compliance. For example, the range of electrical coupling for the relatively more compliant smooth atrial wall is different from the relatively less compliant pectinated myocardial tissue. The level of contact and electrical coupling are often critical to form sufficiently deep ablative lesions on the target tissue 24 without damaging surrounding tissue in the heart 16. The catheter system 10 may be implemented to assess the level of contact (illustrated by display 11) between the electrode catheter 14 and the target tissue 24, as described in more detail below.

Figure 2B:
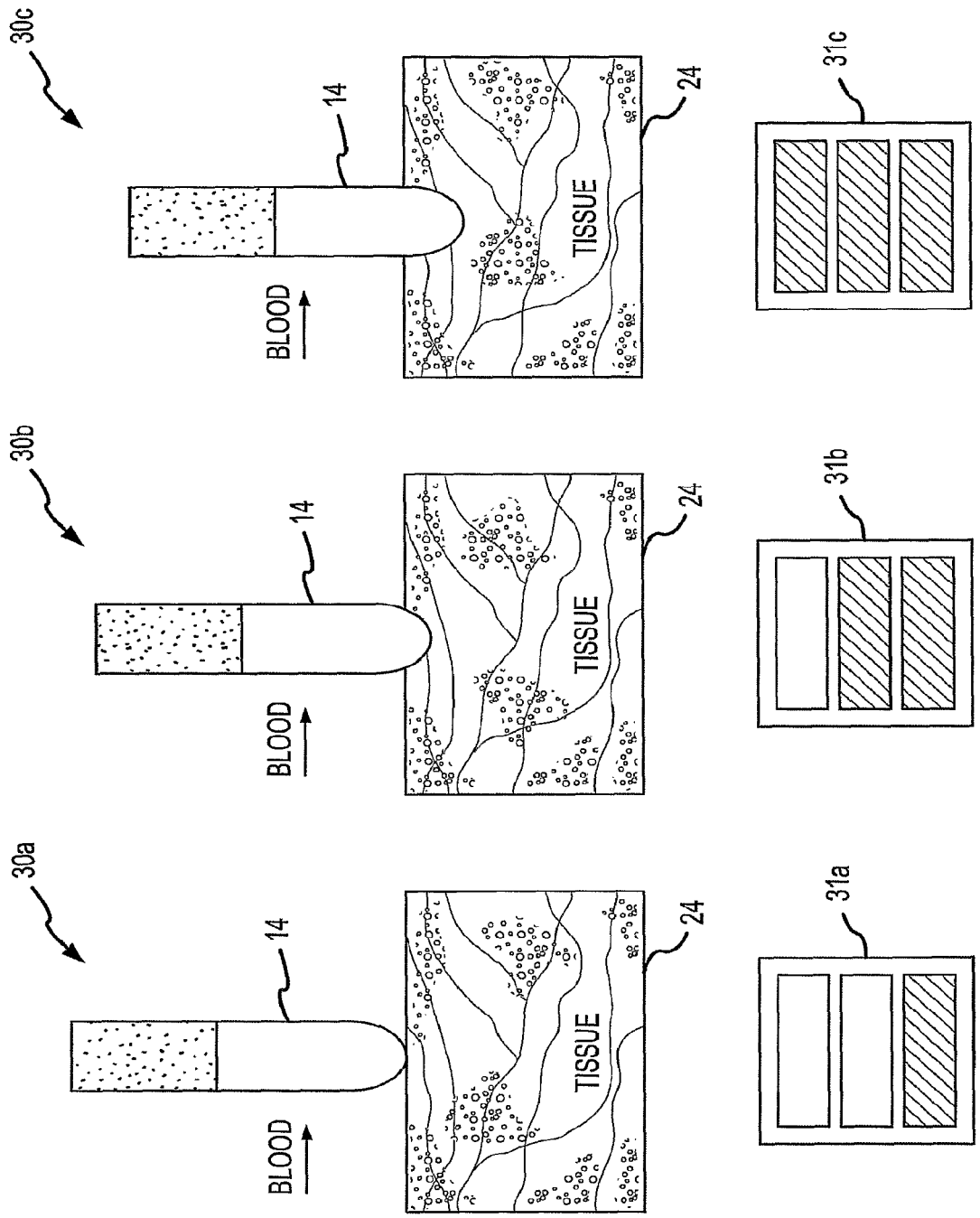
FIG. 2b illustrates exemplary levels of mechanical contact or coupling between the electrode catheter and a target tissue.

FIG. 2a illustrates exemplary levels of electrical contact or coupling between an electrode catheter 14 and a target tissue 24. FIG. 2b illustrates exemplary levels of mechanical contact or coupling between an electrode catheter 14 and a target tissue 24. Exemplary levels of contact or coupling may include "little or no contact" as illustrated by contact condition 30a, "light to medium contact" as illustrated by contact condition 30b, and relatively "hard contact" as illustrated by contact condition 30c. In an exemplary embodiment, the catheter system 10 may be implemented to display or otherwise output the contact condition for the user, e.g., as illustrated by light arrays 31a-c corresponding to contact conditions 30a-c, respectively. While the light arrays 31a-c depict three light levels, any number of light levels may be used to distinguish increasing degrees of contact.

Contact condition 30a ("little or no contact") may be experienced before the electrode catheter 14 comes into contact with the target tissue 24. Insufficient contact may inhibit or even prevent adequate lesions from being formed when the electrode catheter 14 is operated to apply ablative energy. However, contact condition 30c ("hard contact") may result in the formation of lesions which are too deep (e.g., causing perforations in the myocardium 22) and/or the destruction of tissue surrounding the target tissue 24. Accordingly, the user may desire contact condition 30b ("light to medium contact").

It is noted that the exemplary contact or coupling conditions 30a-c in FIG. 2a-b are shown for purposes of illustration and are not intended to be limiting. Other contact or coupling conditions (e.g., finer granularity between contact conditions) may also exist and/or be desired by the user. The definition of such contact conditions may depend at least to some extent on operating conditions, such as, the type of target tissue, desired depth of the ablation lesion, and operating frequency of the RF radiation, to name only a few examples.

Figure 3:
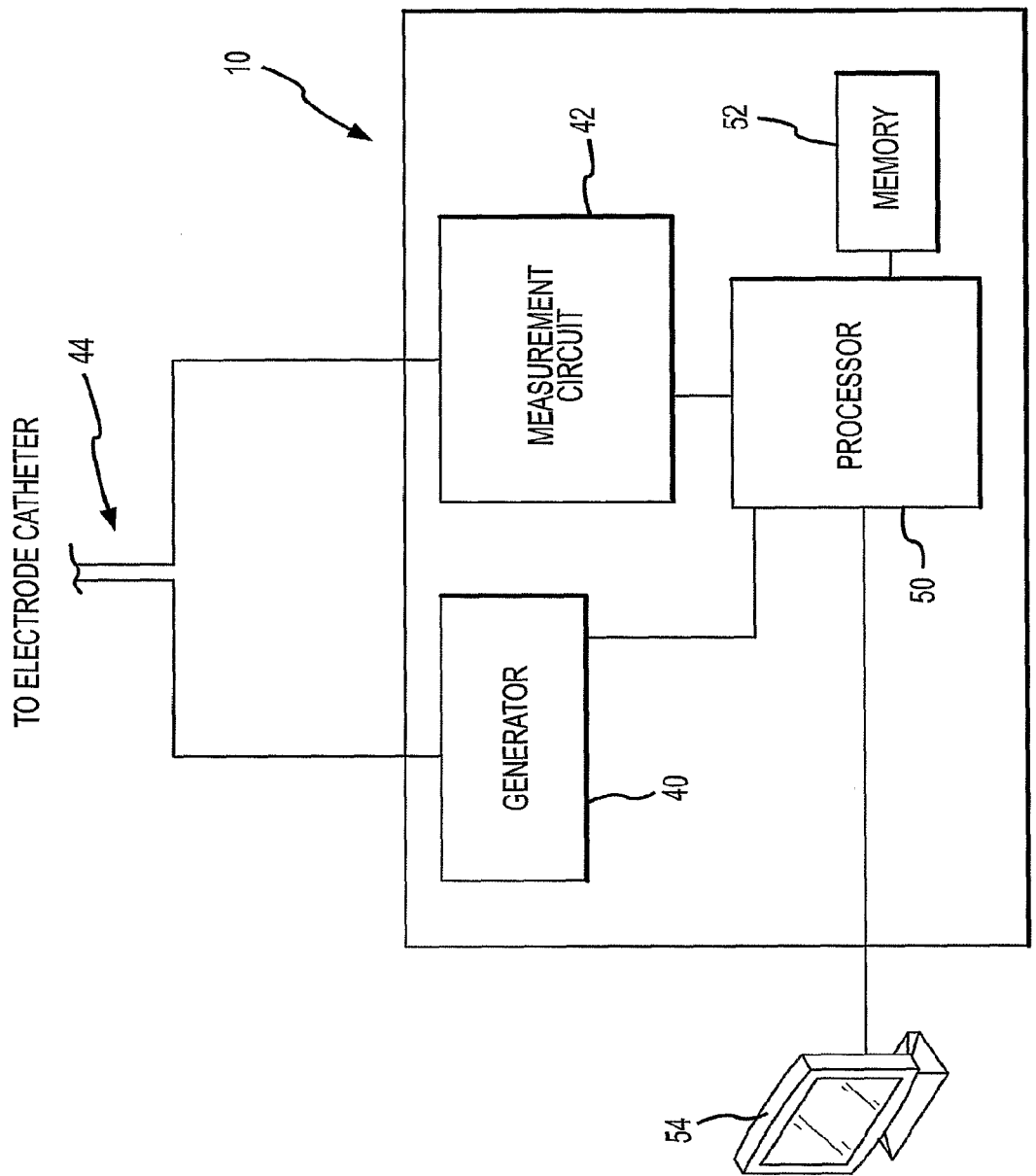
FIG. 3 is a high-level functional block diagram showing the exemplary tissue ablation system of FIG. 1 in more detail.
Figure 4:
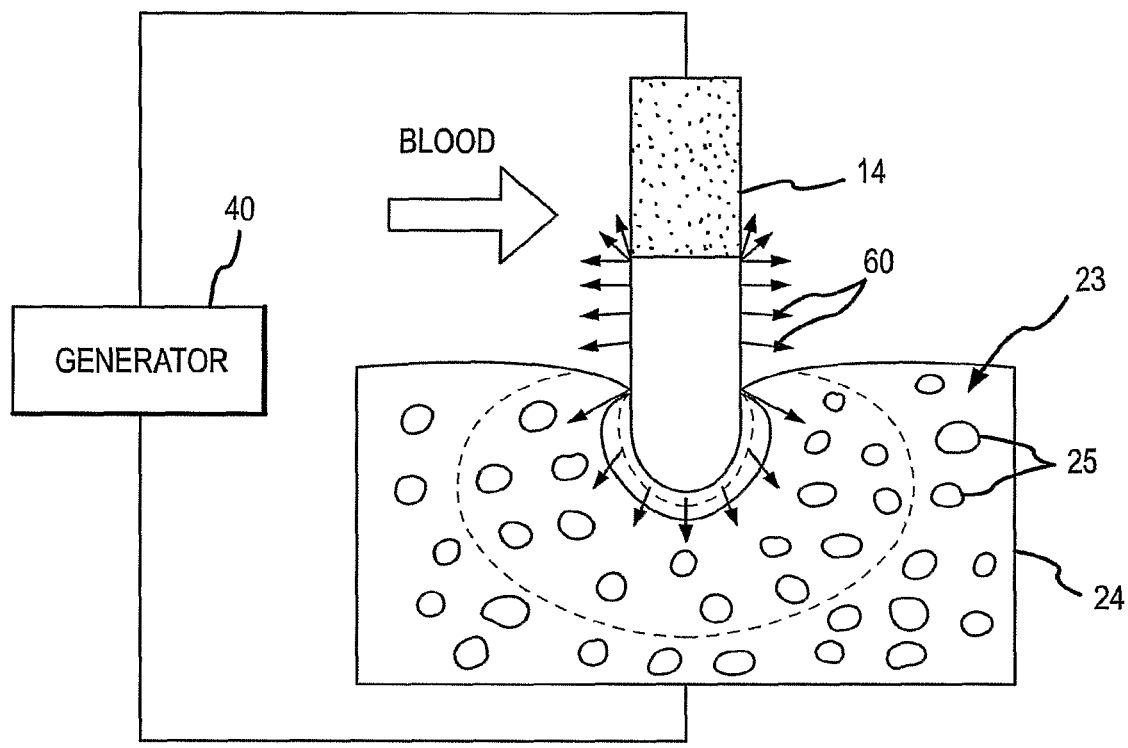
FIG. 4 is a model of the electrode catheter in contact with (or coupled to) target tissue.
Figure 4A:
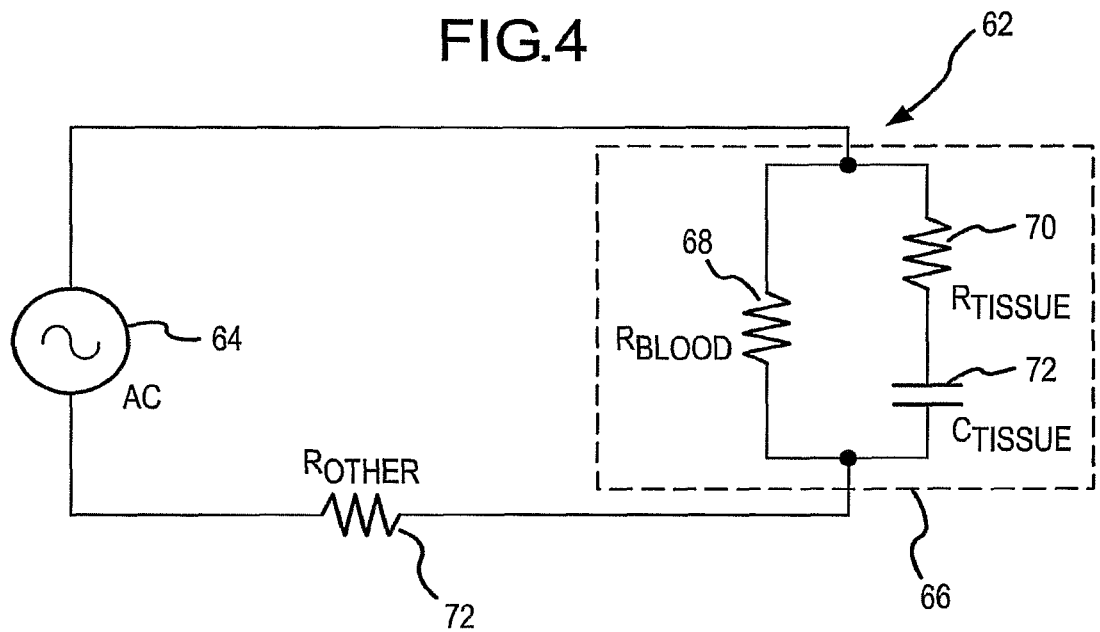
FIG. 4a is a simplified electrical circuit model corresponding to the model shown in FIG. 4.

FIG. 3 is a high-level functional block diagram showing the catheter system 10 in more detail as it may be implemented to assess contact or coupling conditions for the electrode catheter 14. It is noted that some of the components typical of conventional tissue ablation systems are shown in simplified form and/or not shown at all in FIG. 1 for purposes of brevity. Such components may nevertheless also be provided as part of, or for use with the catheter system 10. For example, electrode catheter 14 may include a handle portion, a fluoroscopy imaging device, and/or various other controls, to name only a few examples. Such components are well understood in the medical devices arts and therefore further discussion herein is not necessary for a complete understanding of the invention.

Exemplary catheter system 10 may include a generator 40, such as, e.g., a radio frequency (RF) generator, and a measurement circuit 42 electrically connected to the electrode catheter 14 (as illustrated by wires 44 to the electrode catheter). The electrode catheter 14 may also be electrically grounded, e.g., through grounding patch 46 affixed to the patient's arm or chest (as shown in FIG. 1).

Generator 40 may be operated to emit electrical energy (e.g., RF current) near the tip of the electrode catheter 14. It is noted that although the invention is described herein with reference to RF current, other types of electrical energy may also be used for assessing contact conditions.

In an exemplary embodiment, generator 40 emits a so-called "pinging" frequency (e.g., low power) as the electrode catheter 14 approaches the target tissue 24. The "pinging" frequency may be emitted by the same electrode catheter that is used to apply ablative energy for lesion formation. Alternatively, a separate electrode catheter may be used for applying the "pinging" frequency. In such an embodiment, the separate electrode may be in close contact with (or affixed to) the electrode for applying ablative energy so that a contact or coupling condition can be determined for the electrode which will be applying the ablative energy.

The system can be used to assess the electrode-tissue contact as described in greater detail in the following applications: U.S. Application No. 60/748,234; International Application No. PCT/US06/46565; and U.S. application Ser. No. 12/096,070; each of the foregoing applications is hereby incorporated by reference in its entirety, as if fully set forth herein. The applications explain in detail how the contact may be assessed using the phase angle component of impedance measurements, or more simply by measuring the phase change between the pinging voltage signal and the pinging current signal.

The present invention can also be utilized with U.S. application Ser. No. 12/253,637, which application is hereby incorporated by reference in its entirety, as if fully set forth herein. This application describes methods used to determine a coupling index indicative of a degree of contact between an electrode and a tissue wherein the coupling index is calculated from the components of complex impedance, such as resistance, reactance, impedance magnitude, and impedance phase angle. One of ordinary skill will appreciate that the coupling index may be utilized with the teachings of the present invention to estimate lesion characteristics during lesion formation.

After the user has successfully guided the electrode catheter 14 into the desired contact or coupling condition with the target tissue 24, a generator, such as generator 40 or a second generator, may be operated to generate ablative (e.g., high power) energy for forming an ablative lesion or lesions on the target tissue 24. In an exemplary embodiment, the same generator 40 may be used to generate electrical energy at various frequencies both for the impedance measurements (e.g., "pinging" frequencies) and for forming the ablative lesion. In alternative embodiments, however, separate generators or generating units may also be implemented without departing from the scope of the invention.

In an exemplary embodiment, measurement circuit 42 may be operatively associated with a processor 50 and memory 52 to analyze the measured impedance. By way of example, processor 50 may determine a phase angle, and based on the phase angle, the processor 50 may determine a corresponding contact or coupling condition for the electrode catheter 14. In an exemplary embodiment, contact or coupling conditions corresponding to various phase angles may be predetermined, e.g., during testing for any of a wide range of tissue types and at various frequencies. The contact or coupling conditions may be stored in memory 52, e.g., as tables or other suitable data structures. The processor 50 may then access the tables in memory 52 and determine a contact or coupling condition corresponding to impedance measurements based on the reactance component and/or phase angle. The contact or coupling condition may be output for the user, e.g., at display device 54. Processor 50 may comprise a conventional general purpose computer, a special purpose computer, a distributed computer, or any other type of computer. Processor 50 may comprise one or more processors, such as a single central-processing unit, or a plurality of processing units, commonly referred to as a parallel processing environment.

Figure 5:
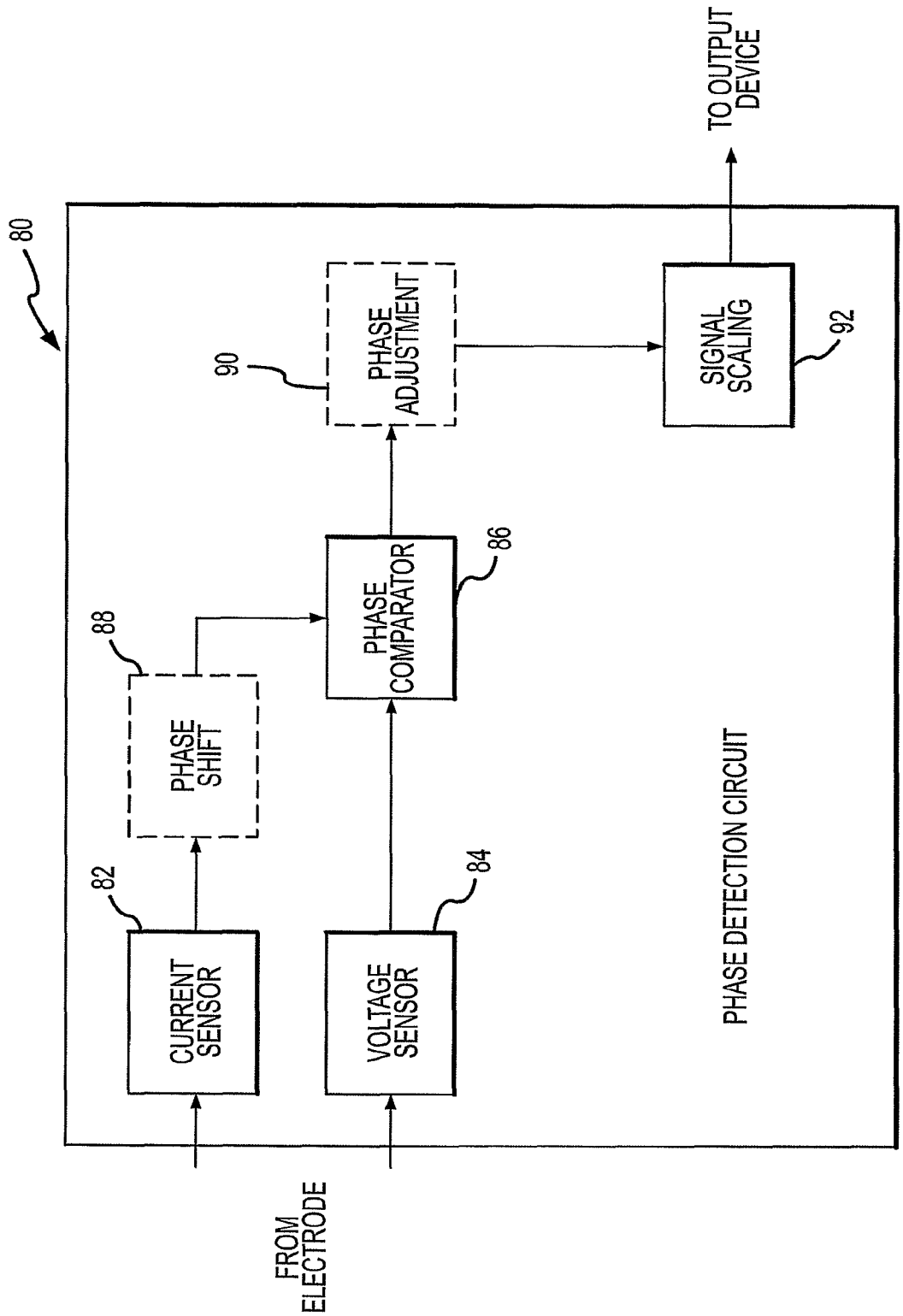
FIG. 5 is an exemplary high level functional block diagram for a phase detection circuit that may be implemented in the tissue ablation system for assessing electrode-tissue contact or coupling.

Although impedance measurements may be used to determine the phase angle, in an alternative embodiment, the measurement circuit 42 may be implemented as a phase detection circuit to directly determine the phase angle. An exemplary phase detection circuit 80 is shown in FIG. 5 in a high-level functional block diagram. Phase detection circuit 80 is shown and described with reference to its functional components. It is noted that a particular hardware configuration is not necessary for a full understanding of the invention. Implementation of the phase detection circuit 80 in digital and/or analog hardware and/or software will be readily apparent to those having ordinary skill in the electronics art after becoming familiar with the teachings herein.

Exemplary phase detection circuit 80 may include a current sensor 82 and voltage sensor 84 for measuring current and voltage at the electrode-tissue interface. The current and voltage measurements may be input to a phase comparator 86. Phase comparator 86 provides a direct current (DC) output voltage proportional to the difference in phase between the voltage and current measurements.

Optionally, current measurements may be phase shifted by phase shift circuit 88 to facilitate operation of the phase comparator 86 by "correcting" phase lag between the measured current and the measured voltage. Also optionally, output from the phase comparator 86 may be "corrected" by phase adjustment circuit 90 to compensate for external factors, such as the type of grounding patch 46 being used. A signal scaling circuit 92 may also be provided to amplify the output (e.g., from milli-volts to volts) for use by various devices (e.g., the processor 50 and display device 54 in FIG. 3).

It is noted that phase detection circuit 80 shown in FIG. 5 is provided as one example, and is not intended to be limiting. Other implementations may also be readily provided by those having ordinary skill in the electronics arts after becoming familiar with the teachings herein without departing from the scope of the invention.

In another exemplary embodiment, measurement circuit 42 as depicted in FIG. 3 includes circuitry to measure voltage and current for different types of power supplies that are used to assess contact between the catheter and tissues being treated.

Measurement circuit 42 also includes temperature measurement circuits that are used to measure and monitor the temperature of the tissue being treated. Measurement circuit 42 utilizes previously described circuitry and/or additional circuitry to measure and monitor power that is delivered by generator 40 and/or by ablation catheter 20.

In an exemplary embodiment, measurement circuit 42 is operatively associated with a processor 50 and memory 52 to analyze degrees of contact or coupling, temperature changes, power and energy. In an exemplary embodiment, processor 50 is programmed to perform regression analysis as described below. Display device 54 may be used to provide feedback to the operator in graphical or numerical form. For example, processor 50 may calculate and display on display device 54 the volume of a lesion as it is being formed. Display device may also display a target lesion volume so that the target may be compared to the size of the lesion being formed. Preferably, processor 50 is programmed to display tissue temperature and to deactivate the ablation power source when the tissue temperature reaches a desired temperature for lesion formation (e.g., about 50-55° C.).

In tissue ablation, a thermal lesion is created when the tissue undergoes coagulation necrosis at temperatures above about 55° C. In radiofrequency (RF) ablation, lesion formation depends upon a number of parameters, such as: (i) electrode-tissue electrical coupling; (ii) the amount of power applied to the electrode from the RF generator; (iii) the duration of power being applied to the electrode by the RF generator; and (iv) the thermal properties and effects of aspects such as (a) the electrode; (b) the tissue; and (c) the fluid around the electrode.

For purposes of this application, "lesion size" is intended to refer to the volume of the lesion being created, and more particularly, the volume of the tissue that underwent coagulation necrosis. Thus, the term "lesion size" is used interchangeably with "lesion volume."

The electrical coupling between the electrode and the tissue refers to the fraction of the electrical energy that flows from the electrode into the tissue. Electrical coupling is effected by: (i) the electrode proximity to or mechanical contact with the tissue; (ii) the size (e.g., surface area) of the electrode; and (iii) the electrical properties of: (a) the electrode; (b) the tissue; and (c) the fluid around the electrode.

Creation of thermally mediated lesion using RF current in tissue is generally described by the bio-heat transfer equation, which in its simplified form may be written as, $$\rho c \frac{\partial T}{\partial t} = \nabla \cdot k \nabla T + JE - Q_h$$

where:
JE is the specific absorption rate ("SAR") of energy applied to the tissue;
$\nabla \cdot k \nabla T$ is the thermal diffusion effect due to thermal conductivity of the tissue;
$Q_h$ is the rate of thermal energy transfer due the convective effects, such as perfusion, blood flow, irrigated cooling;
$\rho c\, \partial T/\partial t$ is rate of energy accumulation in the tissue, which causes the tissue temperature to increase;
T is the tissue temperature;
$\rho$ is the tissue density;
c is the specific heat capacity of the tissue;
$\partial T/\partial t$ is the rate of change in tissue temperature;
J is the electric current density within the tissue;
E is the electric field intensity within the tissue.

The current density J is defined as $$J = i/A,$$

where:
i is the RF current;
A is the area normal to the flow of the current, and is the effective area of electrical coupling between the electrode and tissue.
J is related to the electric field E as, $$J = -\sigma \nabla V = \sigma E,$$

where:
$\sigma$ is the electrical conductivity of the medium;
V is the electrical potential; and
$\nabla V$ is the gradient of electrical potential.
Alternately, SAR may be rewritten as $$JE = |J|^2/\sigma$$
$$= i^2/[A^2 \sigma].$$

Thus an estimation of SAR depends upon the RF current i, the effective area A, and electrical conductivity $\sigma$. In energy dosimetry applications of RF ablation, the electrical conductivity $\sigma$ is a tissue property that is generally known, the RF current i is readily measurable, but A is not readily measurable. The difficulty in measuring A in catheter-based cardiac ablation application is further compounded by: the compliance of the tissue when the catheter is in physical contact with the heart wall; and the contour of the tissue, such as trabeculated tissue, when the electrode may not necessarily be in physical contact with the heart wall.

The phase angle method of measuring electrical coupling provides the reactance $X_R$ of the tissue to the application of RF energy:

$$X_R = 1/(2\pi f C)$$

where:
f is frequency
C is capacitance, which for parallel plate capacitors is given as $$C = \epsilon A/d$$

where:
$\epsilon$ is permittivity of the medium between the plates
A is the cross sectional area between the plates
d is the distance between the plates.

When the electrode is in contact with or close to the tissue, $\epsilon$ may be taken as the permittivity of the tissue, d may be approximated as the depth in tissue that yields enough strength of the RF field so as to create a lesion. In that respect, A may be taken as the effective area of electrical coupling.

The contact or coupling area is an important parameter in RF ablation. It determines: (i) the current density and energy density at the electrode-tissue interface; and (ii) the portion of RF energy absorbed in the tissue during ablation. High current density and energy density at the electrode-tissue interface increase the susceptibility to coagulum and thrombus formation. Excessive energy absorption leads to tissue charring and increases the risk of perforation.

A measure of electrode contact or coupling area, therefore, has prime clinical significance in RF ablation. Such information will allow customizing ablation parameters at individual sites by titrating power levels and ablation time necessary to create safe lesions.

A technical advantage of the present invention is to provide lesion size feedback to physicians based on the degree of electrode-tissue contact or coupling, the RF power levels being delivered to the tissue, and the duration of the RF ablation treatment.

Another technical advantage of the present invention is to provide lesion feedback on lesion characteristics to physicians based on electro-physiological changes in the tissue as measured during the RF ablation treatment.

In one embodiment, the present invention comprises an ablation catheter system that permits electrical contact sensing. The catheter system includes:
 (i) Circuit to measure RF current signal;
 (ii) Circuit to measure RF voltage signal; and
 (iii) Circuit to measure phase angle between current and voltage.

The present invention determines the degree of contact sensing based on the measurement of phase angle $\Delta\phi$ between the RF voltage signal and the RF current signal or the complex impedance as measured using the measured voltage and current. The phase angle $\Delta\phi$ changes with the level of electrode-tissue contact. Preferably, the phase angle $\Delta\phi$ between the RF voltage signal and the RF current signal is measured before or shortly after the RF energy source is activated, though the phase angle $\Delta\phi$ can be measured at any point in time and be used to assess varying degrees of contact. The phase angle $\Delta\phi$ also changes with tissue temperature, and so, as more ablation energy is delivered to the tissue, reliance upon changes in phase angle $\Delta\phi$ must take into consideration the effect of the increased tissue temperature. Generally speaking, the magnitude of phase angle $\Delta\phi$ increases as the degree of tissue-electrode contact increases.

The RF voltage signal being used to measure the phase angle may be supplied by the same RF power source that provides the ablation energy or may be provided by a separate independent supply. The frequency of the RF energy used to assess the electrical coupling is preferably between about 1 KHz and about 1000 KHz, and more preferably between about 50 KHz and about 500 KHz, and most preferably between about 400 KHz and about 500 KHz. The power of the RF signal needed to assess electrical coupling is much lower than the power levels required for ablation, and preferably is less than about 1 W, and more preferably less than about 0.001 W. The current amperage is also significantly less than is necessary for effective ablation and is preferably less than 10 mA, and more preferably less than about 1 mA.

An alternative approach to the device describe above that determines phase angle by comparing the voltage signal to the current is to use a circuit that measures the complex impedance, which is the complex sum of resistance and reactance. The phase angle of the complex impedance is the same phase angle that would be measured by comparing the voltage signal to the current signal.

Yet another alternative approach to the device described above that determines phase angle by comparing the voltage signal to the current is to use a circuit that measures a coupling index which is calculated from the measured components of complex impedance, such as resistance, reactance, impedance magnitude, and impedance phase angle.

It is contemplated that mechanical contact sensing and/or electromechanical sensing may be utilized in conjunction with the electrical contact sensors described above, including for example, piezoelectric sensors, PVDF (polyvinylidene fluoride) film based sensors, and fiber optic-based opto-mechanical contact sensors. In the case of an electrode that senses contact with a beating heart wall, the electrode sensor generates a dynamic voltage signal. The dynamic voltage signal obtained from these contact sensors exhibit waveform characteristics similar to the EKG signals that cause myocardial contractions. It is also contemplated that piezoresistive sensors and Quantum Tunneling Composite (QTC) based sensors may be used, where the resistance of the sensor changes with the contact pressure of the electrode with the tissue.

Contact sensing is important to the ablation process because delivery of ablation energy is proportional to improved electrode-tissue contact. In other words, electrode-tissue contact dictates the energy absorption in tissue, and it is energy absorption in tissue that results in an increase in tissue temperature. As discussed above, a goal of ablation treatment is to increase the tissue temperature to a point that creates irreversible electro-physiological changes in the tissue in the formation of a lesion. Lesion formation in tissues by thermotherapeutic means is achieved by maintaining the tissue temperature above about 50° C.

The total energy $\xi_a$ in Joules applied by the RF generator at power P Watts for a duration of $t_e$ seconds is $$\xi_a = P \times t_e \tag{1}$$

When this energy is applied to an electrode in an endocardial application, part of this energy, $\xi_t$, is absorbed into the tissue to create the lesion at the target site, while the remainder of the energy, $\xi_b$, is lost to the surrounding blood, tissue, electrolyte, and/or the electrode:

$$\xi_a = \xi_t + \xi_b \tag{2}$$

Alternatively, the portion of applied energy $\xi_a$ absorbed in the tissue $\xi_t$ may be expressed as $$\xi_t = \alpha \xi_a \tag{3}$$

where $\alpha$ is an absorptivity factor with a numerical value between 0 and 1, such that $\alpha=0$ when all the applied energy is lost without any absorption in the tissue; $\alpha=1$ when all the energy is absorbed in the tissue.

As the energy $\xi_t$ is absorbed into the tissue, the temperature of the tissue increases. The energy required to create a lesion of volume $v_l$ may be estimated from $$\xi_l = \rho_l \times v_l \times c_l \times \Delta T \tag{4}$$
$$\approx \rho_l \times v_l \times c_l \times (T_l - 37)$$

where $\rho_l$ is the density of the tissue; $c_l$ is the tissue specific heat at constant pressure; $\Delta T$ is the temperature rise required to cause tissue ablation; $T_l$ is the temperature for coagulation necrosis and is also the tissue temperature at the lesion boundary. The patient's body temperature is 37° C. prior to application of ablation energy.

Expressed in terms of the lesion volume $v_l$, Eq. (4) becomes $$v_l = \frac{\xi_t}{\rho_l \times c_l \times \Delta T} \tag{5}$$
$$\approx \frac{\xi_t}{\rho_l \times c_l \times (T_l - 37)}$$

Substituting $\xi_t$ from Eq. (3) into Eq. (5)

$$v_l = \frac{\alpha \xi_a}{\rho_l \times c_l \times \Delta T} \tag{6}$$
$$\approx \frac{\alpha \xi_a}{\rho_l \times c_l \times (T_l - 37)}$$

Substituting $\xi_a$ from Eq. (1) into Eq. (6)

$$v_l = \frac{\alpha(P \times t_e)}{\rho_l \times c_l \times \Delta T} \quad (7)$$
$$\approx \frac{\alpha(P \times t_e)}{\rho_l \times c_l \times (T_l - 37)}$$

For myocardial tissue $\rho_l = 1200$ kg·m$^{-3}$, $c_l = 3200$ J·kg$^{-1}$·°C.$^{-1}$. Taking the $T_l = 55°$ C., the temperature rise required to cause tissue ablation is $\Delta T \approx (55-37)°$ C., or simply, 18° C. Eq. (7) then reduces to:

$$v_l = \frac{\alpha(P \times t_e)}{1200 \times 3200 \times 18} m^3 \quad (8)$$
$$\approx \frac{\alpha(P \times t_e)}{69.12 \times 10^6} m^3$$
$$\approx 14.47(\alpha \times P \times t_e) \text{mm}^3$$

Eq. (8) shows that the main variables determining lesion volume are (i) power P, (ii) duration $t_e$, and (iii) absorptivity factor $\alpha$.

The absorptivity factor $\alpha$ depends upon a number of factors that mainly include (i) the degree of electrode-tissue contact $\zeta$, (ii) tissue characteristics $\chi$, and (iii) ambient flow conditions $\mathcal{F}$ at the site of the contact:

$$\alpha = f \left\{ \begin{array}{l} \text{Electrode-tissue contact},\\ \text{(Tissue characteristics)},\\ \text{(Flow conditions)},\\ \ldots \end{array} \right\} = f \left\{ \begin{array}{l} \zeta, \chi, \mathcal{F}, \\ \ldots \end{array} \right\} \quad (9)$$

In the absorptivity factor, tissue characteristics and ambient flow conditions at the site of the electrode-tissue contact are physiological parameters. On the other hand, level of contact between the electrode and the tissue is established by the physician, and is, therefore, operator dependent.

Limiting the dependency of the lesion volume to operator dependent variables, Eq. (8) can be rewritten to include the aspects of contact sensing as:

$$v_l \approx 14.47[f_1(\zeta) \times P \times t_e] \text{mm}^3 \quad (10)$$

where $0 \leq f_1(\zeta) \leq 1$.

For RF energy applications, phase change $\Delta\phi$ between the voltage and current is directly related to the level of electrode-tissue contact $$\Delta\phi \Leftrightarrow \zeta \quad (11)$$

The lesion volume can then be related to phase change $\Delta\phi$ due to electrode-tissue contact as $$v_l \approx 14.47[f_2(\Delta\phi) \times P \times t_e] \text{mm}^3 \quad (12)$$

where $0 \leq f_2(\Delta\phi) \leq 1$.

Eq. (12) shows that the lesion volume $v_l$ is a function of three variables:
(i) phase change $\Delta\phi$ due to electrode-tissue contact $\zeta$;
(ii) power P; and
(iii) duration $t_e$.

To determine the functional dependence of any one variable on lesion volume $v_l$ will require multiple data points as part of a validation study. Preferably, the validation study is created using a plurality of lesions in which information may be gained to permit estimation a priori. For ease of concept, a plurality of lesions can be made using various different levels of contact as follows:

Preset power P, i.e. in the power control mode;
Preset duration $t_e$; and
Different levels of contact, such as $\Delta\phi_1, \Delta\phi_2, \ldots \Delta\phi_n$.

As part of the validation study, the ablation system may be operated in power control mode, in which the ablation energy is delivered at a fixed power level. Each of the plurality of different levels of contact is determined by measuring the phase angle $\Delta\phi$ between the RF voltage signal and the RF current signal at a point in time before or shortly after the RF energy source is activated. If the phase angle is measured before the commencement of ablation energy, the changes in phase angle can be more easily compared across the plurality of lesions because each is measured at the same tissue temperature. While the phase measurement may be made shortly after the ablation energy is activated, the measurement is preferably made before any appreciable increase in temperature. Because the phase angle $\Delta\phi$ varies with changes in tissue temperature, once the ablation energy begins to cause an increase in tissue temperature, the impact on the phase angle as a measure of electric coupling will require adjustments.

Generally speaking, in this set-up, only one variable is changing over the creation of the plurality of different lesions, namely the degree of contact (which causes a variation in the phase angle). At the end of each ablation process, for each of the plurality of lesions:

Lesion volume $v_l$ is measured;
Values of $v_l$, P, and $t_e$ are substituted in Eq. (12) to obtain the value of $f_2(\Delta\phi)$; and
Values of $f_2(\Delta\phi)$ are plotted against $\Delta\phi$ and a regression curve $f_{2R}(\Delta\phi)$ is computed.

The volume $v_l$ is measured using known volumetric measurements. For example, in the case of a hypothetical rectangular lesion, volume may be determined by multiplying width by length by depth. Depending on the shape, other formulas and/or measurements may be made using known volumetric techniques. Typically, the length and width of the lesion are in proportion to the electrode size, and accordingly, a lesion depth may be estimated using lesion length and lesion width.

The collection of data points for the validation study is preferably generated, preferably, using a plurality of similar tissue samples. Of course, the tissue samples may be from the same human, multiple humans and/or non-humans. In addition, while the validation study may be completed in advance, the validation study (as well as any regression analysis of the underlying data) may continually be updated using additional data points as they are collected. As one example, the validation study may utilize several hundred data points performed in a pre-clinical animal study, upon which a regression analysis may be performed; additional data points may be added to the study as the additional data points are collected, and the associated regression analysis may be continually updated.

A graph or lookup table for $f_2(\Delta\phi)$ can be generated using a known regression analysis techniques that can be run on the plurality of data points previously collected; the resulting graph of lookup table is referred to as regression curve $f_{2R}(\Delta\phi)$ or, more simply, $f_{2R}(\Delta\phi)$. The $f_{2R}(\Delta\phi)$ data can then be used to provide lesion size feedback in real-time for various power settings such as power control mode operations for various levels of contact or coupling.

For example, once the regression analysis has been completed, lesion size feedback can be provided on future ablation treatment. An ablation catheter may be placed in contact with tissue to be treated, and the degree of electrical coupling can be determined by measuring the phase change $\Delta\phi$ between the voltage and current curves as described above. Using the $f_{2R}(\Delta\phi)$ data embodied in the regression curve, the measured $\Delta\phi$ can be used to determine a value of $f_2(\Delta\phi)$. The determined value $f_2(\Delta\phi)$ can then be substituted into Eq. (12), along with the value of power P, to estimate the size of lesion development $v_l$ as a function of time. This methodology is useful for providing lesion size feedback throughout the ablation process.

The characteristics of a lesion formed during ablation depends upon the electro-physiological changes that occur in the tissue during the ablation process, including for example, the temperature attained by the tissue. The combination of lesion size feedback and tissue temperature is most useful to increasing the efficacy of an ablation treatment, and the present invention provides real-time feedback on the characteristics of the lesion being formed as the surgeon performs the ablation process.

In an exemplary embodiment of the present invention, an ablation catheter of the ablation system is placed in contact with tissue to be treated at a particular level of contact. The degree of contact is determined by applying a first power signal and then measuring the phase angle between the voltage signal and the current signal; alternatively the degree of contact may be determined by measuring the complex impedance using the applied first power signal, and in particular, using the phase angle associated with the complex impedance. Ablation energy is then delivered at the same degree of contact to create a lesion, and the system estimates on a real-time basis the size and other characteristics of the lesion being created by using at least the following: i) information obtained through regression analysis; ii) information related to the degree of contact; iii) information related to the power of ablation energy being delivered; and iv) the amount of time for which the ablation energy has been activated. Optionally, the lesion volume of the lesion being created may be estimated and the treatment time period (for which ablation energy is to be applied) is adjusted based on the estimated lesion volume in an effort to achieve particular lesion characteristics. For example, adjustments may be made to the ablation power source in order to slow the delivery of ablation energy to help reduce the risk of tissue pop.

While the degree of contact is preferably measured before any significant increase in temperature from the delivery of ablation energy (for example, by measuring before the ablation energy is activated), it is contemplated that the degree of contact may be measured throughout the ablation process. Of course, to compare degrees of contact will require adjustments based on changes in tissue temperature. Generally speaking, the phase angle associated with a particular degree of contact will reduce in magnitude as the temperature of the tissue increases.

Accounting for Changes in Tissue Temperature.

Preliminary in vitro studies show that at any contact level, phase angle is also affected by changes in tissue temperature. In other words, phase angle change is a function of tissue temperature as well as electrical coupling—the latter of which was discussed in detail above:

$$\Delta\phi = \Delta\phi(\zeta, \Delta T). \tag{12}$$

Including such effects, Eq. (7) can be recast in a form indicative of electro-physiologic changes in the lesion volume $v_l$ obtained by subjecting the tissue to a temperature increase $\Delta T$; thus $$v_l = \frac{f_2\{\Delta\varphi(\zeta, \Delta T)\} \times P \times t}{\rho_l \times c_l \times \Delta T} \tag{14}$$

In Eq. (14) the lesion volume $v_l$ is volume of the tissue that underwent coagulation necrosis; P is the applied power; t is the duration; $\rho_t$ is the density of the tissue; $c_l$ is the tissue specific heat at constant pressure; $\Delta T$ is the rise in tissue temperature obtained during ablation.

While the previous discussion utilized a fixed power P (such as will occur in a power-controlled mode of ablation), another embodiment of the present invention may be utilized with varying levels of power, such as may occur in a temperature-controlled mode of ablation. In this embodiment, the equations may be modified to account for variations in power as a function of time (which will be adjusted by using the function P(t)). This introduces another variable into the system of equations, which variable requires adjustments in the equations.

Under temperature control mode, the applied power P is generally not constant but varies with time when the preset maximum power is higher than needed to attain the tissue temperature. In that case, the total energy $\xi_a$ applied by the RF generator cannot be expressed as $P \times t_e$. Instead, $\xi_a$ is obtained from the time integral of P as $$\xi_a = \int_0^{t_e} P(t)\,dt \tag{15}$$

Rewriting Eq. (14) for temperature control mode operation $$\begin{aligned}
v_l &= \frac{f_2\{\Delta\varphi(\xi, \Delta T)\} \times \xi_a}{\rho_l \times c_l \times \Delta T} \tag{16} \\
&= \frac{f_2\{\Delta\varphi(\xi, \Delta T)\} \times \int_0^{t_e} P(t)\,dt}{3.84 \times 10^6 \times \Delta T} m^3 \\
&= \frac{260.4 \times f_2\{\Delta\varphi(\xi, \Delta T)\} \times \int_0^{t_e} P(t)\,dt}{\Delta T} mm^3
\end{aligned}$$

In Eq. (16), $\Delta T = (T_{set} - 37)°$ C., where $T_{set}$ is the preset temperature in the temperature control mode; $t_e$ is the duration at the instant when the recorded temperature T first attains $T_{set}$.

Eq. (16) shows that the lesion volume $v_l$ is a function of four variables:
 (i) temperature rise $\Delta T$
 (ii) phase change $\Delta\phi$ due to electrode-tissue contact $\zeta$
 (iii) phase change $\Delta\phi$ due to temperature rise $\Delta T$
 (iv) total applied energy $\xi_a$ To determine the functional dependence of any one variable on lesion volume $v_l$ will require multiple data points as part of a validation study. Preferably, the validation study is created using a plurality of lesions in which information may be gained to permit estimation a priori. For ease of concept, a plurality of lesions can be made using various different levels of contact as follows:

Preset cutoff temperature $T_{set}$, i.e. in the temperature control mode
 Preset maximum power $P_{max}$
 Different levels of contact, such as $\Delta\phi_1, \Delta\phi_2, \ldots \Delta\phi_n$
 At the end of the creation of each of the plurality of lesions:
  At $t = t_e$, phase change $\Delta\phi(\Delta T) = \Delta\phi|_{t=t_e}$ due to temperature rise $\Delta T = (T_{set} - 37)°$ C. is recorded
 Lesion volume $v_l$ is measured
 Values of $v_l$, P(t), $t_e$, and $\Delta T$ are substituted in Eq. (16) to obtain the value of $f_2(\Delta\phi)$ Values of $f_2(\Delta\phi)$ are plotted against $\Delta\phi(\zeta)=\Delta\phi|_{t=0}$ and $\Delta T$ to compute the regression curve $f_{2R}[\Delta\phi(\zeta, \Delta T)]$ The volume $v_l$ is measured using known volumetric measurements. For example, in the case of a hypothetical rectangular lesion, volume may be determined by multiplying width by length by depth. Depending on the shape, other formulas and/or measurements may be made using known volumetric techniques. Typically, the length and width of the lesion are in proportion to the electrode size, and accordingly, a lesion depth may be estimated using lesion length and lesion width.

The collection of data points for the validation study is preferably generated, using a plurality of similar tissue samples. Of course, the tissue samples may be from the same human, multiple humans and/or non-humans. In addition, while the validation study may be completed in advance, the validation study (as well as any regression analysis of the underlying data) may continually updated using additional data points as they are collected. As one example, the validation study may utilize several hundred data points performed in a pre-clinical animal study.

A graph or lookup table for $f_2[\Delta\phi(\zeta, \Delta T)]$ can be generated using a known regression analysis techniques that can be run on the plurality of data points previously collected; the resulting graph of lookup table is referred to as regression curve $f_{2R}[\Delta\phi(\zeta, \Delta T)]$ or, more simply, $f_{2R}[\Delta\phi(\zeta, \Delta T)]$. The $f_{2R}[\Delta\phi(\zeta, \Delta T)]$ data can then be used to provide lesion size feedback in temperature control mode operations for various levels of contact or coupling.

For example, once the regression analysis has been completed, lesion size feedback can be provided on future ablation treatment. An ablation catheter may be placed in contact with tissue to be treated, and the degree of electrical coupling can be determined by measuring the phase change $\Delta\phi$ between the voltage and current curves as described above. Using the $f_{2R}[\Delta\phi(\zeta, \Delta T)]$ data embodied in the regression curve, the measured $\Delta\phi$ can be used to determine a value of $f_2[\Delta\phi(\zeta, \Delta T)]$. The determined value $f_2[\Delta\phi(\zeta, \Delta T)]$ can then be substituted into Eq. (16), along with the monitored information on P(t) and $\Delta T$ to estimate the size of lesion development $v_l$ as a function of time. This methodology is useful for providing lesion size feedback throughout the ablation process.

In an exemplary embodiment of the present invention, an ablation catheter of the ablation system is placed in contact with tissue to be treated at a particular level of contact. The degree of contact is determined by applying a first power signal and then measuring the phase angle between the voltage signal and the current signal; alternatively the degree of contact may be determined by measuring the complex impedance using the applied first power signal, and in particular, using the phase angle associated with the complex impedance. Ablation energy is then delivered at the same degree of contact to create a lesion using a mode of operation in which the ablation power level may vary over time. The system estimates on a real-time basis the size and other characteristics of the lesion being created by using at least the following: i) information obtained through regression analysis; ii) information related to the degree of contact; iii) information related to the total amount of ablation energy being delivered over time, including variations of power over time; and iv) the amount of time for which the ablation energy has been activated. Optionally, the estimation may be based, in part, on changes in tissue temperature, and changes in phase angle due to changes in tissue temperature. The lesion volume of the lesion being created may be estimated and the treatment time period (for which ablation energy is to be applied) may be adjusted based on the estimated lesion volume in an effort to achieve particular lesion characteristics. For example, adjustments may be made to the ablation power source in order to slow the delivery of ablation energy to help reduce the risk of tissue pop.

In an exemplary embodiment of the present invention, a system may be used to estimate treatment times to achieve a lesion having certain characteristics, for example, a lesion with a particular depth.

In another exemplary embodiment of the present invention, a system may be used to estimate lesion characteristics for a given treatment time period. For example, lesion depth may be estimated in real time using the time for which an ablation treatment has been on-going. As discussed above, lesion volume may be estimated as a function of time (namely, the time for which an ablation treatment has been active). Also as discussed above, the length and width of the lesion are in proportion to the electrode size, and can be estimated for any given electrode shape. Once the width and length has been estimated for an electrode (for example, but using a regression analysis on detailed volumetric measurements which include, width, length, depth and a shape factor), lesion depth may be estimated on a real-time basis.

While the degree of contact is preferably measured before any significant increase in temperature from the delivery of ablation energy (for example, by measuring before the ablation energy is activated), it is contemplated that the degree of contact may be measured throughout the ablation process.

One of ordinary skill will appreciate that the coupling index described in U.S. application Ser. No. 12/253,637, referenced and incorporated above, may also be utilized with the teachings of the present invention to estimate absorptivity factor ($\alpha$). The coupling index can be calculated from the components of complex impedance, such as resistance, reactance, impedance magnitude, and impedance phase angle, and can be used to estimate absorptivity as described above. Once an absorptivity factor ($\alpha$) has been estimated, the absorptivity can be used to estimate lesion characteristics, including for example, lesion volume (including width, length, and depth) as well as to estimate time needed to complete treatment in order to achieve lesions having certain characteristics.

While the power source used for ablation is described in certain embodiments above as being an RF power source, the principles of the present invention are applicable to other power sources.

While the power source used for assessing tissue-electrode contact is described in certain embodiments above as being an RF power source, the principles of the present invention can be used with any alternating current power source, including very low frequency, low frequency and high frequency power sources. It is anticipated that the circuits describe above may be modified to accommodate the changes in frequency and to filter out noise that may otherwise be present.

Although several embodiments of this invention have been described above with a certain degree of particularity, those skilled in the art could make numerous alterations to the disclosed embodiments without departing from the spirit or scope of this invention.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An ablation system for ablating tissue in need of treatment, comprising:
    an ablation catheter having at least one electrode,
    a power source coupled to at least one electrode, said power source being programmable to deliver at least one programmable level of power;
    a voltage measurement device for measuring a voltage signal being delivered to the tissue;
    a current measurement device for measuring a current signal being delivered to the tissue;
    a phase measurement device to determine an amount of phase change between the measured voltage signal and the measured current signal;
    a clock to measure a time period during which ablative power is delivered by the power source;
    a lesion analysis processor for estimating lesion formation as a function of at least: the measured phase change between the voltage signal and the current signal; information indicating the programmable power level at which the power source delivers ablative power to tissue in need of treatment; and the measured time period for which ablative power is delivered by the ablation catheter to tissue in need of treatment; and
    a controller coupled to the power source and the lesion analysis processor for controlling the power source based on information provided by the lesion analysis processor.

2. The ablation system of claim 1, further comprising:
    a tissue temperature measurement device to measure a temperature of the tissue being ablated; and
    wherein the controller is coupled to the tissue temperature measurement device such that if the temperature of the tissue being ablated exceeds a maximum desirable temperature, the controller will deactivate the ablation source.

3. The ablation system of claim 1,
wherein
    the lesion analysis processor utilizes a regression analysis of a plurality of previously collected data points to calculate an absorptivity factor for the tissue being ablated,
    each of the plurality of previously collected data points comprises information respectively for a plurality of lesions, including at least a degree of tissue-electrode contact, a lesion volume, and an ablation power level; and
wherein the lesion analysis processor calculates a lesion volume for a lesion being created based on a measured amount of phase change, a programmed level of ablation power being used to create the lesion; and a time period measured by the clock indicating the time for which the ablation treatment has been active.

4. The ablation system of claim 3, wherein the controller is programmed to continue delivering ablation power if the lesion analysis processor determines that the calculated lesion volume for the lesion being created is less than a desired lesion volume.

5. The ablation system of claim 1, wherein the power source is an RF power source and wherein the lesion analysis processor estimates lesion formation as a function based on the measured phase change between an RF voltage signal and an RF current signal at the point in time when the RF power source is initially activated.

6. The ablation system of claim 1, wherein the lesion analysis processor estimates lesion formation as a function based on the measured phase change between the voltage signal and the current signal at the point during treatment when the lesion is being estimated.

7. The ablation system of claim 1, wherein the power source is coupled to a first electrode and is used to deliver ablation energy to the tissue in need of ablation, said system further comprising:
    a second power source coupled to a second electrode on the catheter, said second power source being used to deliver assessment power which will be measured by the voltage measurement device and the current measurement device to assess the degree of contact between the second electrode and the tissue in need of treatment.

8. The ablation system of claim 1, wherein the power source is programmed to deliver assessment power at a level that is below an ablation power level, which assessment power is measured by the voltage measurement device and the current measurement device to assess the degree of contact between the catheter and the tissue in need of treatment, and wherein the power source is also programmed to deliver ablation energy to the tissue in need of treatment.

9. An ablation system for ablating tissue in need of treatment, comprising:
    an ablation catheter having at least one electrode, a power source coupled to at least one electrode, said power source being programmable to deliver at least one programmable level of power;
    a voltage measurement device for measuring a voltage signal being delivered to the tissue;
    a current measurement device for measuring a current signal being delivered to the tissue;
    a contact assessment device that assesses a degree of electrical coupling or contact between the ablation catheter and tissue being treated by determining an amount of phase change between the measured voltage signal and the measured current signal;
    a clock to measure a time period during which ablative power is delivered by the power source;
    a power monitoring device to monitor the amount of ablation power that is delivered by the ablation catheter;
    a temperature sensor to measure the temperature of the tissue being treated and to monitor for changes over time;
    a lesion analysis processor for estimating lesion formation as a function of at least: i) a output of the contact assessment device that corresponds to an amount of phase change between the measured voltage signal and the measured current signal at a point in time before the temperature of the tissue increases from application of ablation energy; ii) information from the power monitoring device indicative of the amount of ablation power that is delivered by the ablation catheter as a function of time; iii) information from the temperature sensor indicative of the changes in temperature of the tissue being treated with ablation energy; and
    a controller coupled to the power source and the lesion analysis processor for controlling the power source based on information provided by the lesion analysis processor.

10. The ablation system of claim 9, wherein the controller is coupled to the tissue temperature measurement device such that if the temperature of the tissue being ablated exceeds a maximum desirable temperature, the controller will deactivate the power source.

11. The ablation system of claim 9, wherein the lesion analysis processor includes a look up table or graph of a regression analysis of previously measure lesion volumes for a plurality of lesions, and the lesion analysis processor calculate an absorptivity factor for the tissue being ablated, which absorptivity factor is also used by the lesion analysis processor to estimate lesion formation.

12. The ablation system of claim 9, wherein the controller is programmed to operate the power supply at a first power level to allow the system to assess electrical coupling or contact between the catheter and the tissue and a second power level to ablate tissue.

13. An ablation system for ablating tissue in need of treatment, comprising:
    an ablation catheter having at least one electrode to deliver ablation energy to tissue in need of treatment,
    a variable power source coupled to at least one electrode;
    a voltage measurement device for measuring a voltage signal being delivered to the tissue;
    a current measurement device for measuring a current signal being delivered to the tissue;
    a phase measurement device to determine an amount of phase change between the measured voltage signal and the measured current signal;
    a power measurement device to measure, as a function of time, the power being delivered by the power source;
    a lesion analysis processor for estimating lesion formation as a function of at least: a measured phase change between the voltage signal and the current signal; and information indicating an amount of power that is delivered to the tissue.

14. The ablation system of claim 13 wherein the lesion analysis processor estimates an amount of treatment time necessary to form a lesion.

15. The ablation system of claim 13 wherein the lesion analysis processor provide real-time feedback on an estimated depth of a lesion being created using the system.

* * * * *